United States Patent
Ullattumpoyil et al.

(10) Patent No.: US 11,280,778 B2
(45) Date of Patent: Mar. 22, 2022

(54) DETERMINING CHEMICAL OXYGEN DEMAND

(71) Applicant: Saudi Arabian Oil Company, Dhahran (SA)

(72) Inventors: Nasir Ullattumpoyil, Abqaiq (SA); Abdulaziz M. Rueshed, Abqaiq (SA)

(73) Assignee: Saudi Arabian Oil Company, Dhahran (SA)

( * ) Notice: Subject to any disclaimer, the term of this patent is extended or adjusted under 35 U.S.C. 154(b) by 44 days.

(21) Appl. No.: 16/939,824

(22) Filed: Jul. 27, 2020

(65) Prior Publication Data
US 2020/0355666 A1    Nov. 12, 2020

Related U.S. Application Data

(63) Continuation of application No. 15/986,404, filed on May 22, 2018, now Pat. No. 10,725,011.

(51) Int. Cl.
*G01N 33/18* (2006.01)
(52) U.S. Cl.
CPC ................ *G01N 33/1806* (2013.01)
(58) Field of Classification Search
CPC ................................................. G01N 33/1806
See application file for complete search history.

(56) References Cited

U.S. PATENT DOCUMENTS

| | | | |
|---|---|---|---|
| 5,667,754 A | 9/1997 | Brayton et al. | |
| 2017/0001893 A1* | 1/2017 | Gurney | C02F 1/385 |

FOREIGN PATENT DOCUMENTS

| | | |
|---|---|---|
| WO | 1997012240 | 4/1997 |
| WO | 2016106048 | 6/2016 |

OTHER PUBLICATIONS

Chen et al., "Rapid Determination of Chemical Oxygen Demand (COD) Using Focused Microwave Digestion Followed by a Titrimetric Method," The Japan Society for Analytical Chemistry, Analytical Sciences, Apr. 2001, 17:551-553 , 3 pages.

Geerdink et al., "A reliable mercury free chemical oxygen demand (COD) method," Analytical Methods vol. 1, The Royal Society of Chemistry, Sep. 2009, 7 pages.

Kayaalp et al., "A new approach for chemical oxygen demand (COD) measurement at high salinity and low organic matter samples," Environmental Science Pollution Resource, May 17, 2010, 6 pages.

Li et al., "Analytical Approaches for Determining Chemical Oxygen Demand in Water Bodies: A review," Critical Reviews in Analytical Chemistry, Taylor & Fracis Group, available on or before Oct. 30, 2017, 19 pages.

(Continued)

*Primary Examiner* — Jennifer Wecker
*Assistant Examiner* — Michael Paul Shimek
(74) *Attorney, Agent, or Firm* — Fish & Richardson P.C.

(57) ABSTRACT

A chemical oxygen demand (COD) of a sample including water is determined. At least two test specimens are obtained. Each of the test specimens include a mixture of the sample and a standard solution including potassium hydrogen phthalate (KHP) in a known concentration. Each of the specimens include a same amount of the sample. Each of the specimens include different amounts of the standard solution. Each of the specimens is diluted with water. A COD of each of the specimens is measured. A COD of the sample is determined based on the measured CODs of the specimens.

10 Claims, 7 Drawing Sheets

(56) References Cited

OTHER PUBLICATIONS

Liu et al., "Chemical Oxygen Demand of Seawater determined with a microwave heating method," Journal of Ocean University of China, Apr. 2005, 4(2), 5 pages.

Sato et al., "Determination of Low-Range COD with Cr(VI)-Cr(III)-Hg(II) for Samples of High Concentration Chloride," The Japan Society for Analytical Chemistry, Analytical Sciences, proceedings of the IUPAC International Congress on Analytical Sciences (ICAS 2001), Aug. 6-10, 2001, 17(Suppl.), 2 pages.

Vyrides and Stuckey, "A modified method for the determination of chemical oxygen demand (COD) for samples with high salinity and low organics," Bioresource Technology, Sep. 2008, 100, 5 pages.

GCC Examination Report in GCC Appln. No. GC 2019-37612, dated Jun. 11, 2020, 3 pages.

PCT International Search Report and Written Opinion in International Appln. No. PCT/US2019/031958, dated Sep. 17, 2019, 14 pages.

GCC Examination Report in GCC Appln. No. GC 2019-37612, dated Oct. 11, 2020, 3 pages.

\* cited by examiner

DETERMINING CHEMICAL OXYGEN DEMAND

CROSS-REFERENCE TO RELATED APPLICATIONS

This application claims priority to U.S. application Ser. No. 15/986,404, filed on May 22, 2018, the entire contents of which are incorporated herein by reference.

TECHNICAL FIELD

This disclosure relates to determination of pollutants, for example, organic pollutants, in aqueous samples.

BACKGROUND

Oxygen demand is a parameter that can be used to assess the concentration of organic pollutants in water resources. As microorganisms in the environment consume these materials, oxygen is depleted from the water. Chemical oxygen demand (COD), biological oxygen demand (BOD), and total organic carbon (TOC) are three indices that can be used to assess the level of organic pollution in aqueous systems. TOC analysis can be used for organic compounds, and BOD can be used to reflect biodegradable portions of the pollutants. COD is commonly used to represent the pollution level of waste waters. COD can be defined as the amount of oxygen consumed in the oxidation of organic compounds by strong oxidizing agents.

SUMMARY

This disclosure describes technologies relating to determination of chemical oxygen demand (COD) of aqueous samples.

Certain aspects of the subject matter described here can be implemented as a method for determining COD of a sample including water. Step (a): At least two test specimens are obtained. Each of the test specimens include a mixture of the sample and a standard solution including potassium hydrogen phthalate (KHP) in a known concentration. Each of the specimens include a same amount of the sample. Each of the specimens include different amounts of the standard solution. Each of the specimens is diluted with water. Step (b): A COD of each of the specimens is measured. Step (c): A COD of the sample is determined based on the measured CODs of the specimens.

This, and other aspects, can include one or more of the following features.

Measuring the COD of each of the specimens at step (b) can include performing a small scale sealed-tube COD (ST-COD) method.

The ST-COD method can be performed without using mercuric sulfate.

Determining the COD of the sample at step (c) can include obtaining a linear regression on a data set. The data set can include the measured CODs of the specimens and the respective amounts of the standard solution in each of the specimens. Determining the COD of the sample at step (c) can include determining a y-intercept of the linear regression.

The known concentration of KHP in the standard solution can be in a range between 100 parts per million (ppm) and 2,000 ppm.

Each of the specimens can be diluted with water by a factor of at least 2.

Each of the specimens can be diluted with water by a factor of at least 5.

Each of the specimens can be diluted with water by a factor of at least 10.

Each of the specimens can be diluted with water by a factor at which, for each of the specimens, a chloride ion concentration is less than 1,000 milligrams per liter.

A recovery method can be conducted to verify the determined COD of the sample. The sample can be a first sample. Step (d): A second sample can be obtained. The second sample can include a mixture of the first sample and the standard solution. (Step (e)) A COD of the second sample is determined based on the determined COD of the first sample at step (c) and the known concentration of KHP in the standard solution. Step (f): Steps (a), (b), and (c) can be repeated on the second sample. Step (g): The COD of the second sample determined at step (e) can be compared to the COD of the second sample determined at step (f).

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

International Organization for Standardization (ISO) 15705:2002 describes the photometric method for the determination of COD using the small-scale sealed-tube method (ST-COD). The test is empirical and is applicable to any aqueous sample, which includes all sewage and waste waters. The method outlined in ISO 15705:2002 is applicable to undiluted samples having ST-COD values up to 1,000 milligrams per liter (mg/L) and a chloride concentration not exceeding 1,000 mg/L. Samples with higher ST-COD values can be pre-diluted. For samples with low COD, the precision of the measurement may be reduced and the detection limit may be poorer. The method outlined in ISO 15705:2002 oxidizes almost all types of organic compounds and most inorganic reducing agents. The method outlined in ISO 15705:2002 has a detection limit of 6 mg/L for photometric detection at wavelength of 600 nanometers (nm) and titrimetric techniques using a commercial test kit with a range up to 1,000 mg/L COD. The titrimetric portion of the method outlined in ISO 15705:2002 is applicable to samples exhibiting an atypical color or turbidity after the digestion stage.

High concentrations of chloride ions (for example, exceeding 1,000 mg/L) can interfere with COD measurement because the chloride ions can be oxidized by the oxidizing agent used to measure the COD, leading to errors in estimating the amount of organic material in the sample. Additionally, chloride can react with silver sulfate, which negatively impacts the catalytic activity of the silver sulfate used in COD measurements. In cases where a sample has a low COD (for example, less than 20 mg/L) and high chloride concentration (for example, exceeding 1,000 mg/L), various methods have been used to improve accuracy of COD measurement. The interference of chloride ions in COD measurement can be reduced (but not eliminated) by addition of mercuric sulfate, which binds to the chloride ions as a soluble chloromercurate(II) complex. Mercuric sulfate, however, is also a hazardous substance, so avoiding the addition of such hazardous material would be beneficial in consideration of health and safety.

The methods described here modifies the ST-COD method and can be used to determine COD of aqueous samples with any chloride concentration and any level of organic content. The methods described here can be used to accurately determine COD of aqueous samples with high chloride concentration up to 40 grams per liter (g/L) and organic content less than 20 mg/L. The methods described here do not require any additional mercuric sulfate which is hazardous, as some other methods for similar applications require.

Figure 1:
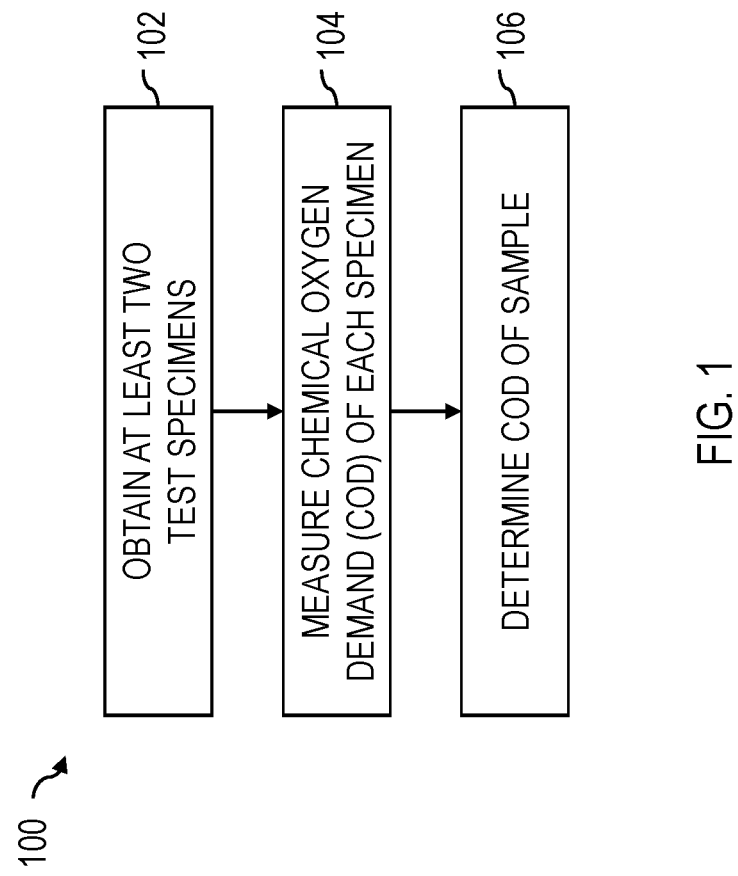
FIG. 1 is a flow chart of a method for determining chemical oxygen demand (COD) of a sample.

FIG. 1 shows a flow chart of an example of a method 100 for determining COD of an aqueous sample (that is, a sample that includes water). Examples of sources of the aqueous sample include, but are not limited to, seawater, groundwater, connate water, produced water, and wastewater. As one example, the aqueous sample can be a sample obtained from a treated water stream from a water treatment plant, and the COD of the sample can be measured to monitor the cleaning efficiency of the water treatment plant. At 102, at least two test specimens are obtained. Each of the test specimens includes a mixture of the sample and a standard solution which includes potassium hydrogen phthalate (KHP) in a known concentration. Because KHP is readily oxidized by the oxidizer used in the ST-COD method (described later), the addition of the standard solution to the sample (in each of the test specimens) can effectively increase the COD level detected in the test specimens. The known concentration of KHP in the standard solution can be in a range between 100 parts per million (ppm) and 2,000 ppm. For example, the standard solution can have a known KHP concentration of 100 ppm or 1,000 ppm. Each of the specimens include the same amount of the sample. For example, each of the test specimens can include 1 milliliter (mL) of the sample. Each of the specimens include different amounts of the standard solution. For example, a test specimen can include 0.25 mL of the standard solution, and another test specimen can include 0.5 mL of the standard solution. The amount of standard solution added to the test specimens depends on various factors, such as the known KHP concentration of the standard solution, initial guess of COD of the aqueous sample, and the extent of dilution of the test specimens in order to mitigate chloride ion interference. The amount of standard solution added to the test specimens can increase by the same increment. For example, 0.2 mL of standard solution is added to a first test specimen, 0.4 mL of standard solution is added to a second test specimen, 0.6 mL of the standard solution is added to a third test specimen, and continuing on (increasing by an additional 0.2 mL of the standard solution) for the remaining test specimens. In some implementations, the amount of standard solution is no more than double the amount of the sample in each of the test specimens.

Each of the specimens are diluted with water. The water used to dilute the specimens can be, for example, distilled water, or any water that has a contamination level (of contaminants such as organic material or molecular species) that is substantially the same or less than that of distilled water. The dilution by water can lower the potential interference of COD measurement by chloride ions that may be present in the sample. Each of the specimens can be diluted with water by a factor at which, for each of the specimens, a chloride ion concentration is less than 1,000 mg/L. Each of the specimens are diluted with water by the same factor. Because the standard solution is added to each of the test specimens, the COD level in each of the test specimens can still remain at a detectable level even after dilution with water. In some implementations, each of the specimens are diluted with water by a factor of at least 2. In some implementations, each of the specimens are diluted with water by a factor of at least 5. In some implementations, each of the specimens are diluted with water by a factor of 10. Each of the specimens can be diluted with water, such that the chloride ion concentration in each of the specimens is less than 1,000 mg/L, and the COD level in each of the test specimens still remain at a detectable level even after dilution with water. The factor of dilution with water can also depend on the concentration of KHP in the standard solution. For example, for standard solutions with KHP concentration greater than 1000 ppm, the specimens can be diluted with water by a factor greater than 10.

Figure 2:
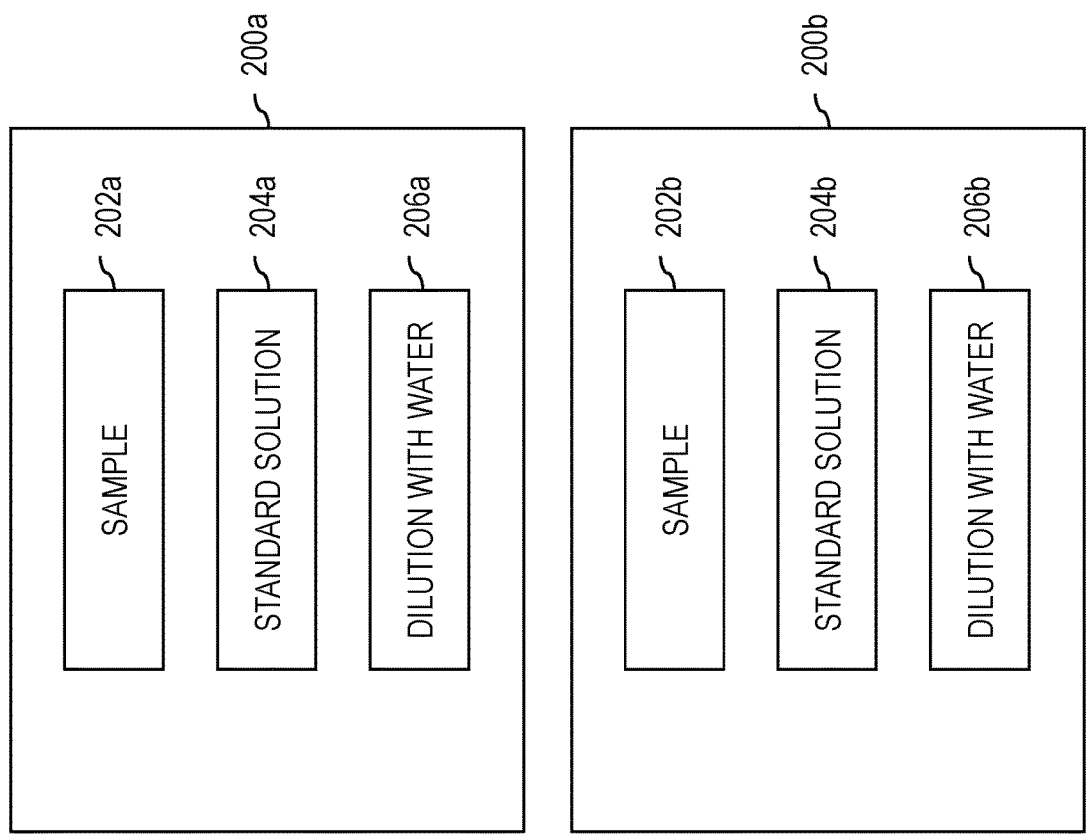
FIG. 2 is a block diagram of test specimens of the method shown in FIG. 1.

FIG. 2 shows a block diagram of examples of test specimens 200a (first) and 200b (second). Each of the test specimens 200a and 200b include an amount of the sample (202a and 202b, respectively). The amount of the sample 202a in the first test specimen 200a is the same as the amount of the sample 202b in the second test specimen 200b. Each of the test specimens 200a and 200b include an amount of the standard solution (204a and 204b, respectively). The amount of the standard solution 204a in the first test specimen 200a is different from the amount of the standard solution 204b in the second test specimen 200b. The test specimens (200a, 200b) are diluted with water (206a, 206b). The amounts of water 206a and 206b used to dilute the test specimens 200a and 200b, respectively, can be the same or different. For example, distilled water can be added to each of the test specimens 200a and 200b, such that the resulting total volumes of the test specimens 200a and 200b are 3 mL each. Then each of the test specimens 200a and 200b can be diluted with distilled water by a factor of 10; in other words, 27 mL of distilled water can then be added to each of the test specimens 200a and 200b, resulting in the test specimens 200a and 200b having a total volume of 30 mL each. Although shown in FIG. 2 as two specimens (200a, 200b), additional test specimens can be included. Additional test specimens (with varying amounts of standard solution) may improve the accuracy of the method 100.

Referring back to FIG. 1 at 104, a COD of each of the specimens is measured. Measurement of COD involves measuring the extent of sample oxidation, which can be affected by such factors as digestion time, reagent strength, and initial sample COD concentration. The measurement is carried out by oxidation of organic compounds into carbon dioxide by using an oxidizing agent at high temperature in an acidic environment. Test specimens can be oxidized by digestion with sulfuric acid and potassium dichromate in the presence of silver sulfate (catalyst) and mercury(II) sulfate (mask chloride ion interference). The organic compounds oxidize, reducing the dichromate ion ($Cr_2O_6^{2-}$). The amount of potassium dichromate used in the oxidation of the test specimens is determined by measuring the absorbance of trivalent (III) chromium ion ($Cr^{3+}$) formed at a wavelength of 600 nanometers (nm)±20 nm for ranges of COD up to 1000 mg/L. Absorbance measurements are conducted on digestion tubes (which functions as a cuvette) and values are converted to ST-COD values. For reduced COD levels (for example, up to 150 mg/L), a reduced calibration range at a wavelength of 440 nm±20 nm may be used to measure the absorbance of hexavalent (VI) chromium ions ($Cr^{6+}$).

Measuring the COD of each of the specimens can be carried out by following a small scale sealed-tube COD (ST-COD) method. The ST-COD method is described in Method 8000 (for measuring water, wastewater, and seawater) by Hach Company and is reproduced (in part) here. First, the test specimen is homogenized for 2 minutes in a blender. A digestion reactor is preheated to 150 degrees Celsius (° C.). A digestion reagent vial (already containing some catalyst and reagent) is held at a 45-degree angle while 2 milliliters (mL) of the test specimen is pipetted into the vial. The vial is capped, and the outside of the vial is rinsed with deionized water and wiped clean and dry. The vial is gently inverted several times to mix the contents. A blank is prepared with 2 mL of deionized water. The vial containing the test specimen and the blank are heated for 2 hours at 150° C. in the digestion reactor. The digestion reactor is turned off, and the vials are left to sit and cool for about at least 20 minutes, so that the vials can cool to 120° C. or cooler. The vials are gently inverted several times while they are still warm and then left to cool to room temperature. The blank can be used to calibrate the colorimeter. Then the vial containing the digested test specimen can be run in the colorimeter to measure the absorbance, which will be converted into a ST-COD measurement by the colorimeter.

At 106, a COD of the sample is determined based on the CODs of the specimens measured at 104. Determining the COD of the sample can include obtaining a linear regression on a data set that includes the measured CODs of the specimens (from 104) and the respective amounts of the standard solution in each of the specimens. As mentioned before, additional test specimens (that is, more than two specimens) can improve the accuracy of the method 100. A linear regression is a linear approach for describing the relationship between a dependent variable y and an independent variable x. Determining the COD of the sample can include determining a y-intercept of the linear regression. The y-intercept is a point where the graph of a relation intersects the y-axis of the coordinate system, and as such, is a point that satisfies x=0. In this context, x=0 represents zero addition of standard solution and effectively represents the COD level of the sample.

Figure 3:
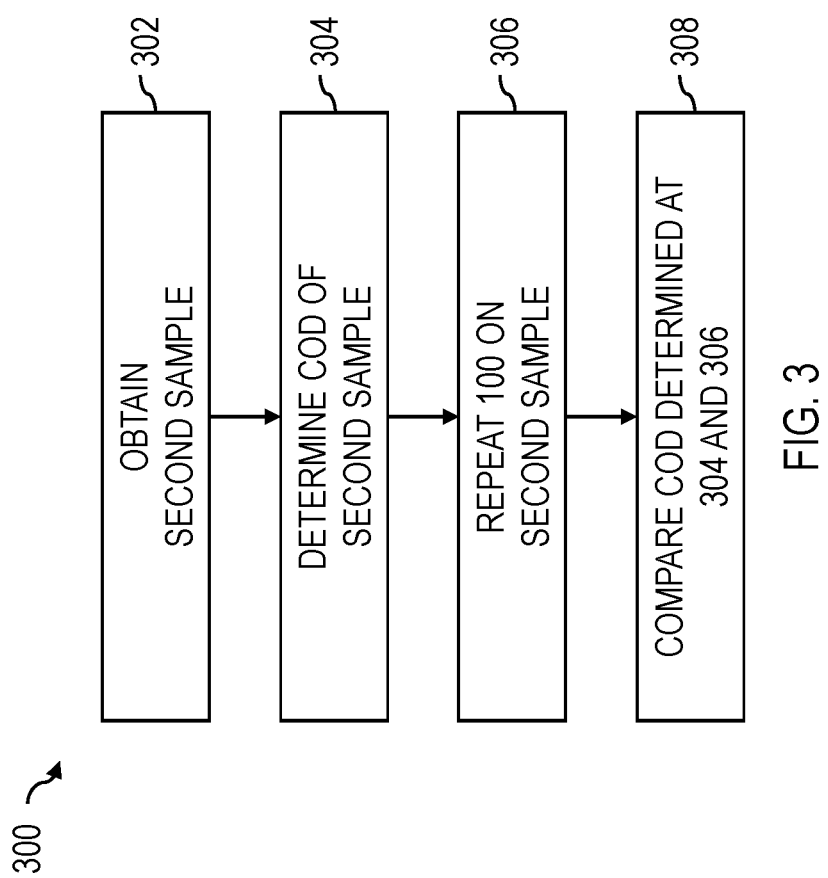
FIG. 3 is a flow chart of a method for verifying a COD determined by the method shown in FIG. 1.

FIG. 3 shows a flow chart of an example of a recovery method 300 to verify the COD of the sample determined at 106 of method 100. The sample in method 100 can be considered a first sample. The recovery method 300 can include obtaining a second sample at 302. The second sample can include a mixture of the first sample and the standard solution. The second sample can include a relatively small amount of the standard solution in comparison to the first sample. The purpose of adding the standard solution is to increase the COD level by a known amount, so that the accuracy of the method 100 can be verified. For example, an amount of standard solution is added, such that the resulting COD of the second sample (for example, calculated by Equation (1) shown later) is less than 10 times the COD of the first sample determined earlier by method 100.

At 304, a COD of the second sample is determined based on the COD of the first sample determined at 106 of method 100 and the known concentration of KHP in the standard solution. The COD of the second sample can be calculated by Equation (1).

$$COD_{second\ sample} = \frac{COD_{standard} \times Volume_{standard} + COD_{first\ sample} \times Volume_{first\ sample}}{Total\ Volume} \quad (1)$$

At 306, steps 102, 104, and 106 of method 100 are repeated on the second sample. The COD calculated using Equation (1) at 304 can be compared with the COD that is determined at 306. At the repeated step 102, at least two test specimens of the second sample are obtained. Each of the test specimens include the same amount of the second sample and varying amounts of the standard solution. The purpose of adding varying amounts of standard solution to the specimens is to increase the COD level of the specimens by varying amounts. Each of the specimens can be diluted with water to mitigate chloride ion interference in COD measurement. At repeated step 104, the COD of each of the specimens is measured, for example, by following the ST-COD method. At repeated step 106, the COD of the second sample is determined based on the CODs that were measured at repeated step 104. The CODs of the test specimens measured at repeated step 104 and their respective amounts of standard solution can be included in a data set, and a linear regression of that data set can be obtained. The y-intercept of the linear regression represents the COD level at zero addition of the standard solution, so the y-intercept can be determined to be the COD of the second sample.

At 308, the COD of the second sample determined at 306 (at the repeated step 106 of method 100 on the second sample) to the COD calculated using Equation (1) at 304. The percent error between the COD values (the COD calculated by Equation (1) assumed as the "true" value) is related to the accuracy of the method 100; less error means more accurate. Error can be calculated by Equation (2).

$$\%\ error = \frac{True\ value - Measured\ value}{True\ value} \times 100\% \quad (2)$$

For example, an error that does not exceed 10% can be considered to be sufficiently accurate.

Example 1

For the method 100, a data set included a measured COD of 20 mg/L for test specimen 1 with 0.5 mL of standard solution and a measured COD of 36 mg/L for test specimen 2 with 1 mL of standard solution. A linear regression on the data set with independent variable x as amount of standard solution in test specimen and dependent variable y as measured COD of test specimen was be y=32x+4. The y-intercept of the linear regression was 4 mg/L, so the COD of the sample (first) was determined to be 4 mg/L.

For the recovery method 300, the second sample included 99.6 mL of the first sample and 0.4 mL of the standard solution (resulting in a ratio of 249:1). The COD of the first sample was determined to be 4 mg/L, and the concentration of KHP in the standard solution was known to be 1,000 ppm. For water, 1 ppm is approximately 1 mg/L, so the COD of the second sample was calculated by Equation (1) as: ((1000 mg/L)×(0.4 mL)+(4 mg/L)×(99.6 mL))/(100 mL)=7.98 mg/L.

The COD was determined to be 8.06 mg/L at the repeated step 106 of method 100 on the second sample, and then the percent error was calculated by Equation (2) as: ((7.98 mg/L)−(8.06 mg/L))/(7.98 mg/L)×100%=−1.0%.

Example 2

Figure 4:
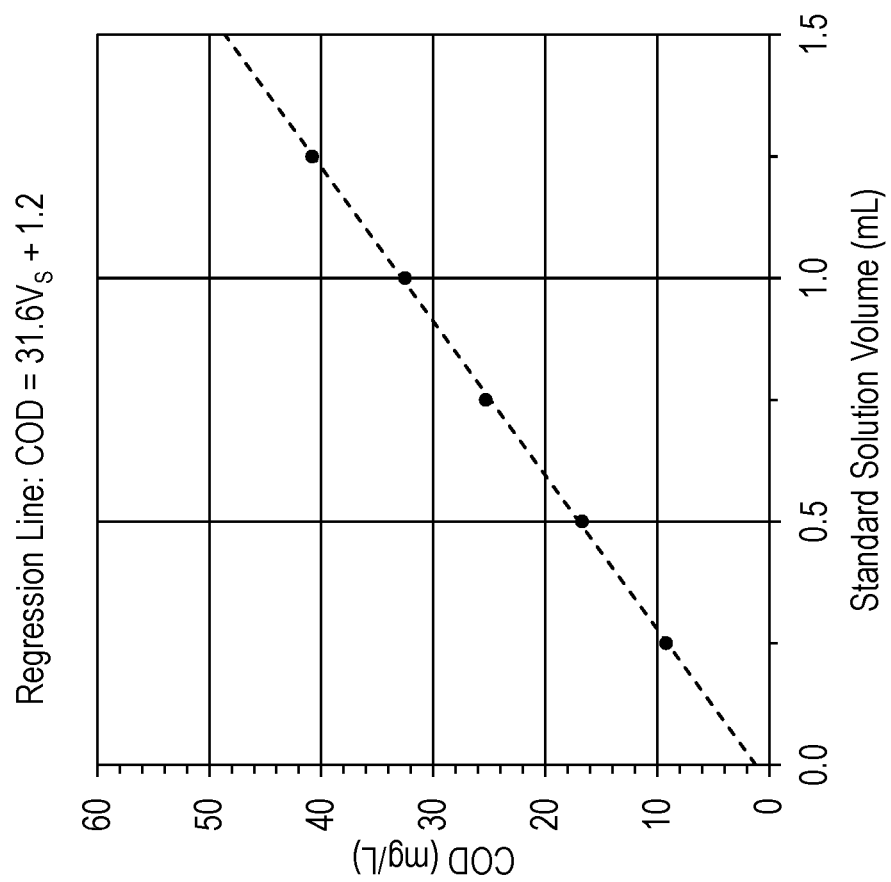
FIG. 4 is a plot showing COD values for various test specimens prepared from an aqueous sample.

FIG. 4 shows a plot of measured COD values vs. volume of standard solution for various test specimens of Example 2. The test specimens were prepared, and their COD values were measured according to method 100 described before. The equation for linear regression of the data set shown in the plot of FIG. 4 was COD=31.6$V_s$+1.2. The COD of the sample was determined to be 1.2 mg/L, the y-intercept of the linear regression. Additional details of the test specimens are provided in Table 1. For each of the test specimens shown in Table 1, distilled water was added to the mixture of the sample and standard solution to reach the total volume, and then each of the specimens were diluted by the factor shown.

TABLE 1

| Test specimen | Sample volume (mL) | Standard solution* volume (mL) | Total volume (mL) | Dilution** (factor) | Measured COD (mg/L) |
|---|---|---|---|---|---|
| 1 | 1 | 0.25 | 3 | 10 | 9.2 |
| 2 | 1 | 0.5 | 3 | 10 | 16.7 |
| 3 | 1 | 0.75 | 3 | 10 | 25.3 |
| 4 | 1 | 1.0 | 3 | 10 | 32.5 |
| 5 | 1 | 1.25 | 3 | 10 | 40.8 |

*Standard solution KHP concentration was 1,000 ppm.
**Dilution with distilled water.

Example 3

Figure 5:
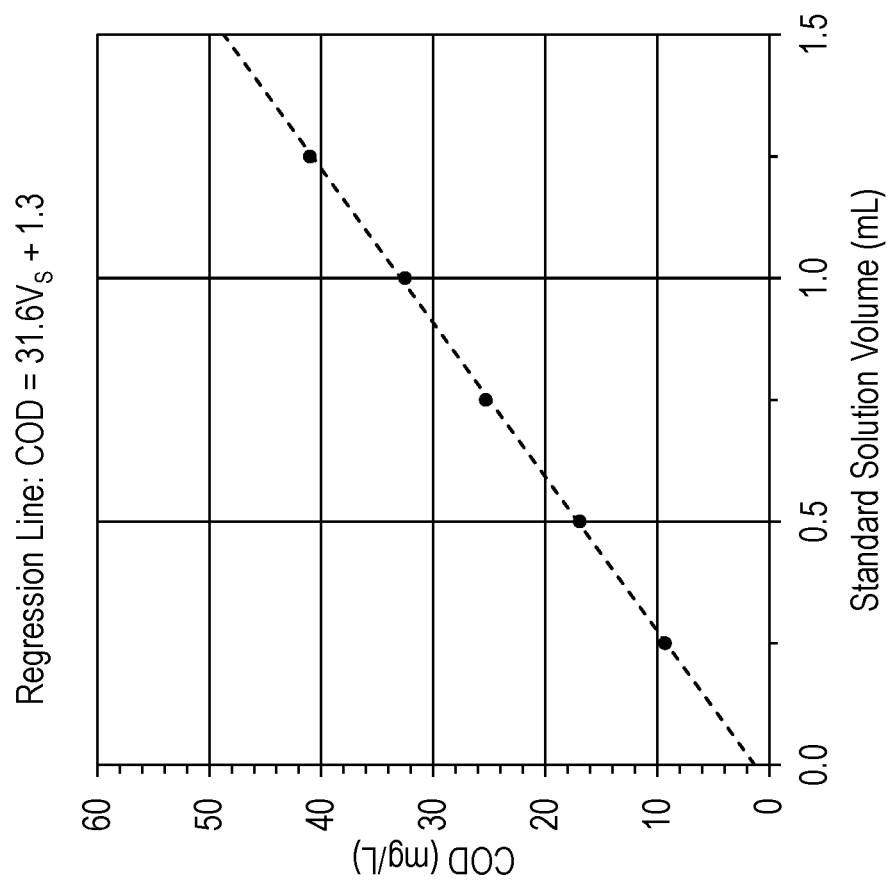
FIG. 5 is a plot showing COD values for various test specimens prepared from an aqueous sample.

FIG. 5 shows a plot of measured COD values vs. volume of standard solution for various test specimens of Example 3. The test specimens were prepared, and their COD values were measured according to method 100 described before. The equation for linear regression of the data set shown in the plot of FIG. 5 was COD=31.6$V_s$+1.3. The COD of the sample was determined to be 1.3 mg/L, the y-intercept of the linear regression. Additional details of the test specimens are provided in Table 2. For each of the test specimens shown in Table 2, distilled water was added to the mixture of the sample and standard solution to reach the total volume, and then each of the specimens were diluted by the factor shown.

TABLE 2

| Test specimen | Sample volume (mL) | Standard solution* volume (mL) | Total volume (mL) | Dilution** (factor) | Measured COD (mg/L) |
|---|---|---|---|---|---|
| 1 | 1 | 0.25 | 3 | 10 | 9.3 |
| 2 | 1 | 0.5 | 3 | 10 | 16.9 |
| 3 | 1 | 0.75 | 3 | 10 | 25.3 |
| 4 | 1 | 1.0 | 3 | 10 | 32.5 |
| 5 | 1 | 1.25 | 3 | 10 | 41.0 |

*Standard solution KHP concentration was 1,000 ppm.
**Dilution with distilled water.

Example 4

Figure 6A:
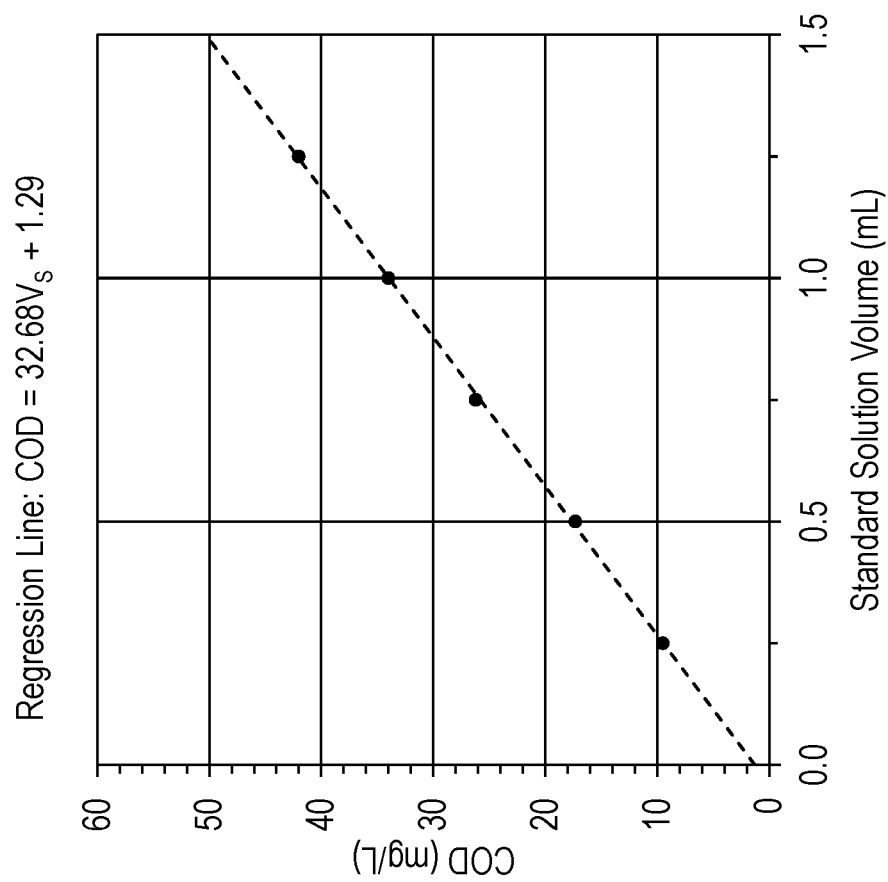
FIG. 6A is a plot showing COD values for various test specimens prepared from an aqueous sample.

FIG. 6A shows a plot of measured COD values vs. volume of standard solution for various test specimens of Example 4. The test specimens were prepared, and their COD values were measured according to method 100 described before. The equation for linear regression of the data set shown in the plot of FIG. 6A was COD=32.68$V_s$+1.29. The COD of the sample was determined to be 1.29 mg/L, the y-intercept of the linear regression. Additional details of the test specimens are provided in Table 3. For each of the test specimens shown in Table 3, distilled water was added to the mixture of the sample and standard solution to reach the total volume, and then each of the specimens were diluted by the factor shown.

TABLE 3

| Test specimen | Sample volume (mL) | Standard solution* volume (mL) | Total volume (mL) | Dilution** (factor) | Measured COD (mg/L) |
|---|---|---|---|---|---|
| 1 | 1 | 0.25 | 3 | 10 | 9.5 |
| 2 | 1 | 0.5 | 3 | 10 | 17.3 |
| 3 | 1 | 0.75 | 3 | 10 | 26.2 |
| 4 | 1 | 1.0 | 3 | 10 | 34.0 |
| 5 | 1 | 1.25 | 3 | 10 | 42.0 |

*Standard solution KHP concentration was 1,000 ppm.
**Dilution with distilled water.

Figure 6B:
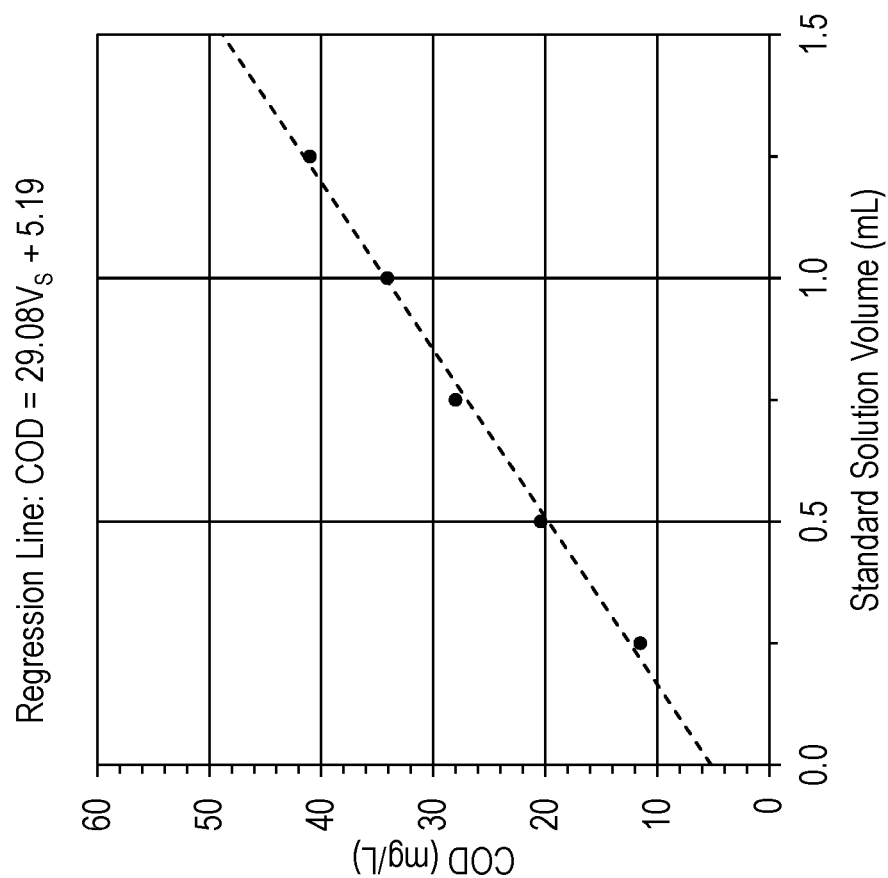
FIG. 6B is a plot showing COD values for various test specimens prepared from the aqueous sample of FIG. 6A.

FIG. 6B shows a plot of measured COD values vs. volume of standard solution for various test specimens of Example 4. The recovery method 300 was performed to verify the accuracy of the method 100 used to produce the results shown in FIG. 6A. The same sample whose results are shown in Table 3 and FIG. 6A was used. 99.6 mL of the sample (first) was mixed with 0.4 mL of the standard solution to form a second sample. Using the COD of the first sample (1.29 mg/L, determined before with results shown in FIG. 6A) and the known concentration of KHP in the standard solution (1 ppm 1 mg/L), the COD of the second sample was calculated using Equation (1): ((1000 mg/L)× (0.4 mL)+(1.29 mg/L)×(99.6 mL))/(100 mL)=5.29 mg/L.

The test specimens were prepared, and their COD values were measured according to the recovery method 300 described before. The equation for linear regression of the data set shown in the plot of FIG. 6B was COD=29.08$V_s$+ 5.19. The COD of the sample was determined to be 5.19 mg/L, the y-intercept of the linear regression. Assuming the "true" value was 5.29 mg/L calculated before using Equation (1), the percent error of the determined COD 5.19 mg/L was calculated using Equation (2): ((5.29 mg/L)−(5.19 mg/L))/(5.29 mg/L)×100%=1.9%. The percent error confirms the accuracy of the method 100. Additional details of the test specimens are provided in Table 4. For each of the test specimens shown in Table 4, distilled water was added to the mixture of the sample and standard solution to reach the total volume, and then each of the specimens were diluted by the factor shown.

TABLE 4

| Test specimen | Sample volume (mL) | Standard solution* volume (mL) | Total volume (mL) | Dilution** (factor) | Measured COD (mg/L) |
|---|---|---|---|---|---|
| 1 | 1 | 0.25 | 3 | 10 | 11.5 |
| 2 | 1 | 0.5 | 3 | 10 | 20.4 |
| 3 | 1 | 0.75 | 3 | 10 | 28.0 |

TABLE 4-continued

| Test specimen | Sample volume (mL) | Standard solution* volume (mL) | Total volume (mL) | Dilution** (factor) | Measured COD (mg/L) |
|---|---|---|---|---|---|
| 4 | 1 | 1.0 | 3 | 10 | 34.1 |
| 5 | 1 | 1.25 | 3 | 10 | 41.0 |

*Standard solution KHP concentration was 1,000 ppm.
**Dilution with distilled water.

While this disclosure contains many specific implementation details, these should not be construed as limitations on the scope of the subject matter or on the scope of what may be claimed, but rather as descriptions of features that may be specific to particular implementations. Certain features that are described in this disclosure in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example implementations do not define or constrain this disclosure. Other changes, substitutions, and alterations are also possible without departing from the spirit and scope of this disclosure.

What is claimed is:

1. A method for determining chemical oxygen demand (COD) of a sample comprising water, the method comprising:
    (a) measuring a COD of a first specimen, the first specimen comprising a mixture of the sample and a first amount of a standard solution comprising potassium hydrogen phthalate (KHP) in a known concentration;
    (b) measuring a COD of a second specimen, the second specimen comprising a mixture of the sample and a second amount of the standard solution, the second amount different from the first amount; and
    (c) determining a COD of the sample based on the measured CODs of the first specimen and the second specimen.

2. The method of claim 1, wherein measuring the COD of each of the first specimen and the second specimen comprises performing a small scale sealed-tube COD (ST-COD) method.

3. The method of claim 2, wherein the ST-COD method is performed without using mercuric sulfate.

4. The method of claim 3, wherein determining the COD of the sample comprises:
    obtaining a linear regression on a data set comprising the measured CODs of the first specimen and the second specimen and the respective amounts of the standard solution in each of the first specimen and the second specimen; and
    determining a y-intercept of the linear regression.

5. The method of claim 4, wherein the known concentration of KHP in the standard solution is in a range between 100 parts per million (ppm) and 2,000 ppm.

6. The method of claim 5, wherein each of the first specimen and the second specimen are diluted with water by a factor of at least 2.

7. The method of claim 6, wherein each of the first specimen and the second specimen are diluted with water by a factor of at least 5.

8. The method of claim 7, wherein each of the first specimen and the second specimen are diluted with water by a factor of 10.

9. The method of claim 5, wherein each of the first specimen and the second specimen are diluted with water by a factor at which, for each of the specimens, a chloride ion concentration is less than 1,000 milligrams per liter.

10. The method of claim 5, further comprising conducting a recovery method to verify the determined COD of the sample, wherein the sample is a first sample, and the recovery method comprises:
    (d) obtaining a second sample, the second sample comprising a mixture of the first sample and the standard solution;
    (e) determining a COD of the second sample based on the determined COD of the first sample at step (c) and the known concentration of KHP in the standard solution;
    (f) repeating steps (a), (b), and (c) for the second sample; and
    (g) comparing the COD of the second sample determined at step (e) to the COD of the second sample determined at step (f).

* * * * *